United States Patent
Grzegorczyk et al.

(10) Patent No.: US 9,255,893 B2
(45) Date of Patent: Feb. 9, 2016

(54) APPARATUS FOR ILLUMINATING SUBSTRATES IN ORDER TO IMAGE MICRO CRACKS, PINHOLES AND INCLUSIONS IN MONOCRYSTALLINE AND POLYCRYSTALLINE SUBSTRATES AND METHOD THEREFORE

(75) Inventors: Wojciech Grzegorczyk, Brussels (BE); Kristiaan Van Rossen, Bierbeek (BE); Johan De Greeve, Brabant (BE); Dominique Janssens, Antwerp (BE)

(73) Assignee: KLA-Tencor Corporation, Milpitas, CA (US)

( * ) Notice: Subject to any disclaimer, the term of this patent is extended or adjusted under 35 U.S.C. 154(b) by 593 days.

(21) Appl. No.: 13/376,480

(22) PCT Filed: Apr. 18, 2011

(86) PCT No.: PCT/IB2011/051656
§ 371 (c)(1),
(2), (4) Date: Dec. 6, 2011

(87) PCT Pub. No.: WO2012/143753
PCT Pub. Date: Oct. 26, 2012

(65) Prior Publication Data
US 2012/0262566 A1 Oct. 18, 2012

(51) Int. Cl.
*H04N 7/18* (2006.01)
*G01N 21/95* (2006.01)
*G01N 21/00* (2006.01)
*G01N 21/88* (2006.01)
*G06T 7/00* (2006.01)

(52) U.S. Cl.
CPC ............ *G01N 21/9505* (2013.01); *G01N 21/00* (2013.01); *G01N 21/88* (2013.01); *G06T 7/0004* (2013.01); *H04N 7/183* (2013.01); *G01N 21/8806* (2013.01); *G06T 2207/30148* (2013.01); *G06T 2207/30164* (2013.01)

(58) Field of Classification Search
CPC ... G01N 21/00; G01N 21/88; G01N 21/9505; G01N 21/8806; G06T 7/0004; G06T 2207/30148; G06T 2207/30164; H04N 7/183
See application file for complete search history.

(56) References Cited

U.S. PATENT DOCUMENTS

| 5,367,174 A | * | 11/1994 | Bazile et al. ............. 250/559.45 |
| 2004/0246476 A1 | * | 12/2004 | Bevis et al. ................ 356/237.5 |
| 2007/0181180 A1 | | 8/2007 | Chou et al. |
| 2007/0188743 A1 | | 8/2007 | Tanaka et al. |
| 2011/0058161 A1 | | 3/2011 | Hemsendorf et al. |
| 2011/0268344 A1 | * | 11/2011 | Chan ............................ 382/145 |

FOREIGN PATENT DOCUMENTS

| DE | 10146879 A1 | 4/2003 |
| EP | 1092973 A1 | 4/2001 |
| EP | 1801569 A3 | 6/2007 |

OTHER PUBLICATIONS

Fornasiero et al. (English Translation of EP 1956366 A1).*
Gramatke et al. (English Translation of EP 1801569 A2).*

* cited by examiner

*Primary Examiner* — Joseph Ustaris
*Assistant Examiner* — Jill Sechser
(74) *Attorney, Agent, or Firm* — Suiter Swantz pc llo (57) ABSTRACT

An apparatus for illuminating monocrystalline and polycrystalline substrates in order to image micro cracks, pinholes and inclusions in the substrates is disclosed. A first illumination system illuminates a first line of light on the front surface of the substrate. A second illumination system illuminates a second line of light on the front surface of the substrate. The first line of light and the second line of light are oriented transverse to the transport direction (T). The second illumination system is arranged within a 3-dimensional coordinate system such that the substrate is illuminated under a second angle. The arrangement of the second illumination system is comparable to a street lamp. A camera, preferably a camera, is arranged such that it faces the back surface of the substrate. The camera captures light which is transmitted through the substrate from the first illumination system and the second illumination system.

26 Claims, 8 Drawing Sheets

APPARATUS FOR ILLUMINATING SUBSTRATES IN ORDER TO IMAGE MICRO CRACKS, PINHOLES AND INCLUSIONS IN MONOCRYSTALLINE AND POLYCRYSTALLINE SUBSTRATES AND METHOD THEREFORE

FIELD OF THE INVENTION

The present invention relates to an apparatus for illuminating wafers and solar cells in order to image micro cracks, pinholes and inclusions in monocrystalline and polycrystalline wafers and solar cells.

The invention relates as well relates to a method for illuminating wafers and solar cells in order to image micro cracks, pinholes and inclusions in monocrystalline and polycrystalline wafers and solar cells.

BACKGROUND OF THE INVENTION

Monocrystalline and polycrystalline silicon wafers are the base material to produce to manufacture monocrystalline and polycrystalline solar cells, respectively. The production process to manufacture a solar cell from a raw wafer includes various steps, and the costs to manufacture a cell from a raw wafer are approximately as high as the material costs for the wafer. Therefore it is important that only wafers that are free from defects are used in production. Critical defects are penetrating and non-penetrating micro cracks, pinholes and inclusions. Micro cracks can cause breakage of the wafer or solar cell during or after production. After production the solar cell may break while mounted to a solar module or cause failure of a mounted or operating module following warranty claims.

Micro cracks are hard to detect within the polycrystalline structure of a wafer because they resemble the crystalline borders. The cracks are then detected by advanced image processing methods. DE 101 46 879 applies an area scan to take the inspection images. A line scan setup is disclosed in EP 1 801 569.

More recent approaches try to capture inspection images where the polycrystalline structure of the wafer is attenuated while maintaining the contrast of the cracks.

The US-Patent application US 2011/058161 discloses a method for detecting defects in an object. The object is locally illuminated by radiating in light having a wavelength to which the object is transparent. Multiple reflected components of the incident light are detected while the detection of directly transmitted components of the incident light is at least partly avoided and the detection of singly reflected components of the incident light is at least partly avoided. Defects are identified by evaluating intensity differences in the detected components of the incident light.

Methods, apparatuses or set-ups which use the image acquisition that captures the directly transmitted light and then finds the cracks by advanced image processing methods suffer from over or under kill. The reason is that the present defect detection image processing methods are not reliable enough due to the presence of grain boundaries in the polycrystalline silicon images.

SUMMARY OF THE INVENTION

The object of the invention is to create an apparatus which improves the contrast of (non-penetrating and penetrating) micro cracks, pin holes and inclusions in silicon substrates such that robust and automatic detection of these defects is possible. More specifically, the invention allows automated inspection of substrates by means of digital processing of images where the polycrystalline boundaries are highly attenuated while maintaining the contrast of the micro cracks, pin holes and inclusions.

This object is achieved by an apparatus for illuminating monocrystalline and polycrystalline substrates in order to image micro cracks, pinholes and inclusions in the substrates. The apparatus has means for moving the substrates at along a transport direction. During the transport of the substrates, a first illumination system illuminates a first elongated spot of light on a front surface of the substrate. The term elongated means that the width of the elongated spot is smaller than the length of the elongated spot. It is preferred that the form of the elongated spot is rectangular. The first spot of light is oriented transverse to the transport direction. The first illumination system illuminates the substrate under a first angle $\alpha$ with respect to the front surface of the substrate. A second illumination system shines a second elongated spot of light on the front surface of the substrate. The second elongated spot of light is oriented transverse to the transport direction, and the second illumination system illuminates the substrate under a second angle $\delta$ with respect to the surface of the substrate. In addition, an axis of the second illumination system is arranged at a third angle $\beta$ with respect to the second elongated spot of light on the front surface of the substrate. An image capture field is assigned to the substrate such that the first elongated spot of light and the second elongated spot of light are mostly outside the image capture field during the movement of the substrates along the transport direction. The term "mostly outside" means as well that the first elongated spot of light and the second elongated spot of light do not intersect the image capture field.

A further object of the invention is to create methods which improve the detection quality of non-penetrating and penetrating micro cracks, pin holes and inclusions in silicon substrates such that robust and automatic detection of these defects is possible.

The above object is achieved by a method for imaging micro cracks, pinholes or inclusions in monocrystalline and polycrystalline substrates comprising the steps of:

(a) moving the substrates along a transport direction;
(b) illuminating a first elongated spot of light on a front surface of a moving substrate, wherein the first elongated spot of light is oriented transverse to the transport direction and the light illuminates the substrate under a first angle $\alpha$ with respect to the front surface of the substrate;
(c) illuminating a second elongated spot of light on the front surface of the substrate wherein the second elongated spot of light is oriented transverse to the transport direction and the light illuminates the substrate under a second angle $\delta$ with respect to the surface of the substrate, and an axis of the second illumination system is arranged at a third angle $\beta$ with respect to the second line on the front surface of the substrate; and
(d) defining an image capture field such that the first elongated spot of light and the second elongated spot of light are mostly outside the image capture field during the movement of the substrate along the transport direction.

In an embodiment, the first and the second illumination system are configured as line light sources. According to a further embodiment, the line light source of the second illumination system is fanned by a plurality of individual line light sources. Each individual line light source shines light onto the substrate under the second angle $\delta$ with respect to the surface of the substrate. The axis of each line light source is arranged at the third angle β with respect to the surface of the substrate.

In a further embodiment, the image capture field is defined by at least one camera. Various camera types, like line scan cameras or area scan cameras, can be used including line scan cameras working in Time Delay Integration (TDI) mode. It is clear to a person skilled in the art that various cameras with various modes of operation can be used in order to practice the invention. The cameras are sensitive to wavebands where the monocrystalline or the polycrystalline substrates are transparent. In a further embodiment, the at least one camera is arranged such that the image capture field is defined on a back surface of the substrate. The at least one camera receives the light from the first illumination system and second illumination system being transmitted through the monocrystalline or polycrystalline substrate.

In a further embodiment, the first illumination system and the second illumination system provide light in a waveband where the monocrystalline and the polycrystalline substrates are transparent.

According to a further embodiment of the invention, two image capture fields are defined by at least a first camera and a second camera. The first camera defines a first image capture field on a back surface of the substrate, and a second camera defines a second image capture field on the back surface of the substrate. The first camera and the second camera receive the light from the first illumination system, and light from the second illumination system is transmitted through the monocrystalline or polycrystalline substrate. In addition, an optical axis of the first camera can be arranged at a fifth angle ε with respect to a normal of the substrate, and an optical axis of the second camera can be arranged at a sixth angle with respect to the normal of the substrate.

According to a further modification of the invention, a third illumination system is arranged such that the second camera captures transmitted light from the third illumination system.

In order to detect light reflected from the front surface of the substrate the image capture field is defined by a camera on a front surface of the substrate in a further embodiment. The camera receives the light reflected from the front surface of the substrate. In this embodiment, the substrate can be a semi or fully finished solar cell with different coatings and metallic electrodes on the front and rear surface.

A further embodiment of the invention is an apparatus for illuminating solar cells and imaging non-penetrating micro cracks in monocrystalline and polycrystalline wafers of semi or fully finished solar cells. The solar cells are transported by means for moving along a transport direction. A first illumination system illuminates a first elongated spot of light on a front surface of the solar cell, the surface including coatings and metallic electrodes. The first elongated spot of light is oriented transverse to the transport direction, and the first illumination system illuminates the solar cell under a first angle α with respect to the front surface of the solar cell. A camera is arranged above the front surface of the solar cell and captures light reflected from the front surface of the solar cell during the movement of the solar cells along the transport direction.

In addition to the first illumination system, a second illumination system is provided for illuminating a second elongated spot of light on the front surface of the solar cell in a further embodiment. The second elongated spot of light is oriented transverse to the transport direction of the substrate. The second illumination system sheds light onto the front surface of the solar cell under a second angle δ with respect to the front surface of the solar cell. An axis of the second illumination system is arranged at a third angle β with respect to the front surface of the solar cell. The camera captures also the light of the second illumination system reflected from the front surface of the solar cell during the movement of the solar cells along the transport direction. The camera is defining an image capture field on the front surface of the solar cell.

A further modification of the apparatus for illuminating and imaging monocrystalline and polycrystalline substrates in order to detect micro cracks, pinholes and inclusions in the substrates includes means for moving the substrates along a transport direction. The apparatus has a first illumination system for illuminating a first elongated spot of light on a front surface of the substrate. The first elongated spot of light is oriented transverse to the transport direction, and the first illumination system illuminates the substrate under a first angle α with respect to the front surface of the substrate. A second illumination system is provided for illuminating a second elongated spot of light on the front surface of the substrate. The second elongated spot of light is oriented transverse to the transport direction. The second illumination system illuminates the substrate under a second angle δ with respect to the surface of the substrate. An axis of the second illumination system is arranged at a third angle β with respect to the front surface of the substrate.

In this modification, a first camera defines a first image capture field, and a second camera defines a second image capture field. The first image capture field and the second image capture field are defined at the back surface of the substrate. The first and the second camera receive the light from the first illumination system. Light from the second illumination system is transmitted through the monocrystalline or polycrystalline substrate.

In a further embodiment of this modification, an optical axis of the first camera is arranged at a fifth angle £ with respect to the normal of the back surface of the substrate. An optical axis of the second camera is arranged at a sixth angle with respect to the normal of the back surface of the substrate. The angle can be 0 degrees (0°). In extreme measurement situations the angles can range between+/−89 degrees (+/−89°).

According to a further embodiment of the invention, a third illumination system is arranged such that the second camera captures transmitted light from the third illumination system through the substrate. The first, the second and the third illumination system can be configured as line light sources.

An image acquisition setup for the detection of micro cracks, pinholes and inclusions in polycrystalline solar cells and wafer comprises at least one camera. The camera captures light transmitted through the wafer or solar cell or reflected from the surface of the wafer or solar cell. A first light source illuminates the wafer or solar cell. The wafer or the solar cell is positioned and oriented such that the image capture field or image capture line of the camera on the wafer or solar cell is mostly outside the areas on the wafer or solar cell where light from the line light source is directly reflected or directly transmitted. The line light source illuminates the wafer or solar cell under a first angle α. A second line light source illuminates the wafer or the solar cell and is positioned and oriented such that the image capture field or image capture line of the camera is mostly outside the areas on the wafer or solar cell where light from the line light source is directly reflected or directly transmitted. The line light source illuminates the wafer or solar cell under a third angle β (like a street lamp). The camera and the light sources operate in wave bands where polycrystalline solar cells and wafers are transparent.

A second camera can be used which captures transmitted light from the first line light source (shining light under the first angle α onto the surface of the wafer or solar cell). The second camera images penetrating cracks, pinholes and inclusions.

BRIEF DESCRIPTION OF THE DRAWINGS

The nature and mode of operation of the present invention will now be more fully described in the following detailed description of the invention taken with the accompanying drawing figures, in which.

DETAILED DESCRIPTION OF THE INVENTION

Same reference numerals refer to same elements throughout the various figures. Furthermore, only reference numerals necessary for the description of the respective figure are shown in the figures. The shown embodiments represent only examples of how the apparatus and methods according to the invention can be designed. This should not be regarded as limiting the invention.

For example, any sequence(s) and/or temporal order of steps of various processes or methods that are described are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Figure 1:
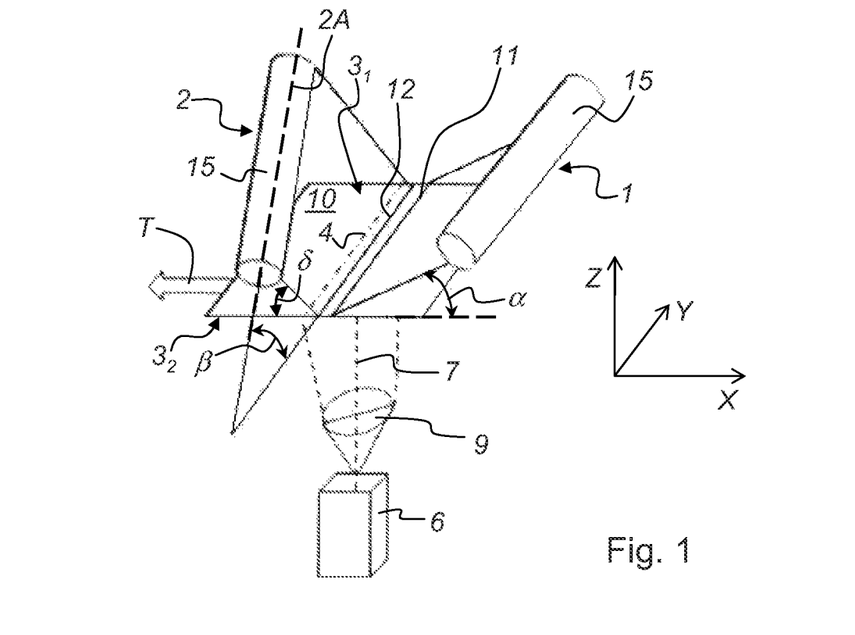
FIG. 1 shows a schematic 3-dimensional view of an embodiment of the set up according to the present invention.

FIG. 1 shows a schematic 3-dimensional view of an embodiment of the invention which is able to overcome the orientation dependency of inspection systems to detect micro cracks in substrates (wafers or solar cells). A first illumination system 1 and a second illumination system 2 are arranged opposite to the front surface 31 of a substrate 10 in order to shine light onto front surface 31 of substrate 10. First illumination system 1 and second illumination system 2 comprise elongated light spot sources 15 respectively.

First illumination system 1 illuminates a first elongated spot 11 of light on front surface $3_1$ of substrate 10. The first elongated spot 11 of light is oriented transverse to a transport direction T of substrate 10, and the light from the first illumination system 1 is directed to the front surface $3_1$ of substrate 10 under a first angle α. The second illumination system 2 illuminates a second elongated spot 12 of light on the front surface $3_1$ of substrate 10. As the first elongated spot 11 of light, also the second elongated spot 12 of light is oriented transverse to transport direction T. The second illumination system 2 is arranged within a 3-dimensional coordinate system (X, Y, Z) such that substrate 10 is illuminated under a second angle δ with respect to the front surface $3_1$ of substrate 10. Furthermore, an axis 2A of the second illumination system 2 is arranged at a third angle β with respect to the front surface $3_1$ of substrate 10. Third angle β ranges between 5 to 30 degrees, but preferably third angle β ranges between 10 to 25 degrees with respect to the second line 12 of light. The arrangement of the second illumination system 2 with third angle β is comparable to a street lamp, which results in a non-homogeneous light intensity distribution across the second elongated spot 12 of light. The arrangement of the first illumination system 1 and the second illumination system 2 is such that the first elongated spot 11 of light and the second line 12 of light do not intersect within substrate 10. A camera 6 is arranged such that it faces the back surface $3_2$ of substrate 10. The camera 6 captures light which is transmitted through substrate 10 from the first illumination system 1 and the second illumination system 2. The camera 6 is sensitive in the wavelength band of 700 to 1800 nm.

An optical system 9 is assigned to camera 6 in order to form an image capture field 4 or scan line to the back surface $3_2$ of substrate 10. The image capture field 4 is arranged such that the first line 11 of light and the second line 12 of light are mostly outside the image capture field 4 during the movement of substrates 10 along transport direction T. Each substrate 10 (wafer or solar cell) to be inspected is being transported along transport direction T. With the constant movement of substrate 10 the first elongated spot 11 of light, the second elongated spot 12 of light, and the capture field 4 pass over the entire front surface $3_1$ and back surface $3_2$ of substrate 10 respectively.

The following description of the invention refers to the image capture field 4 which should not be considered a limitation of the invention. It is evident to any person skilled in the art that image capture field 4 can also have the form of a line.

According to the present invention a substrate 10 (monocrystalline or polycrystalline wafers or semi or fully finished solar cells) is illuminated by a combination of first illumination system 1 and second illumination system 2. Due to the combined illumination the micro cracks in substrate 10 can be imaged in all directions of the X/Y-plane of substrate 10 as shown in FIG. 1.

As mentioned before, the tilted arrangement by third angle β of the second illumination system 2 with respect to the second elongated spot 12 of light generates an inhomogeneous intensity distribution on the front surface $3_1$ of substrate 10 along the illuminated second elongated spot 12 of light. The smaller the distance of second illumination system 2 to substrate 10 is, the brighter the illuminated area of the illuminated second elongated spot 12 of light is. This drawback needs to be compensated for. For example, a camera 6 with high dynamic range may be used. Alternatively, an attenuation filter (not shown) could be used that has a high attenuation where the second illumination system 2 is close to substrate 10 (wafer or solar cell) and low attenuation where the second illumination system 2 is far away from substrate 10. Yet another possibility is to attenuate or dim the light the closer it is to substrate 10 (e.g., if the second illumination system 2 is composed of multiple dimmable light sources). A disadvantage of all these approaches is that the second illumination system 2 is arranged under the third angle β with respect to the second line 12 of light which requires complex optics in order to provide a focused second line 12 of light.

Figure 2:
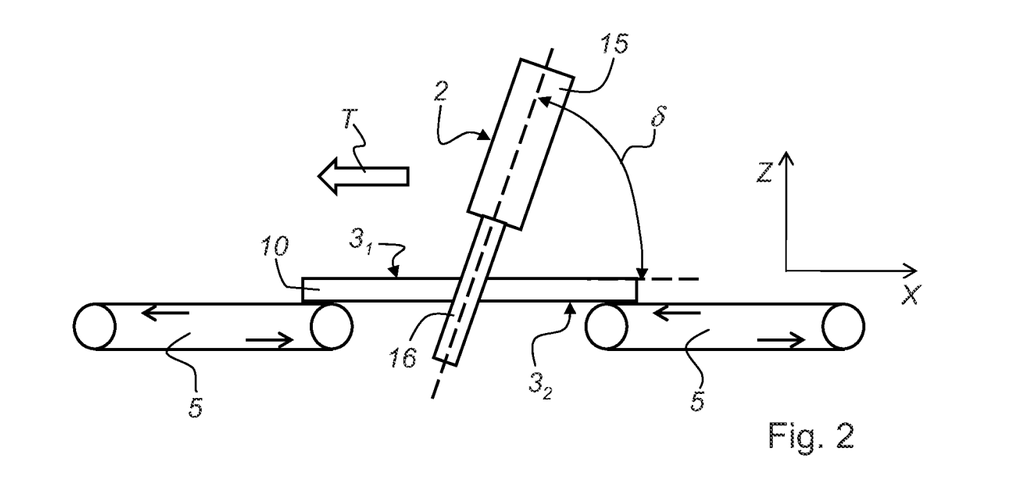
FIG. 2 shows a schematic side view of the arrangement of the second illumination system with respect to the substrate (wafer or solar cell)
Figure 3:
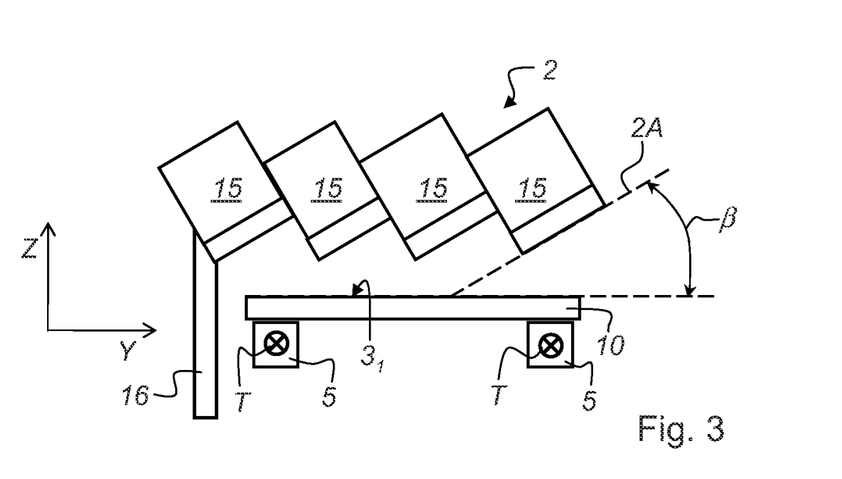
FIG. 3 shows a schematic front view of the arrangement of the second illumination system according to FIG. 2, wherein the transport direction of the substrate is perpendicular to the drawing plane.
Figure 4:
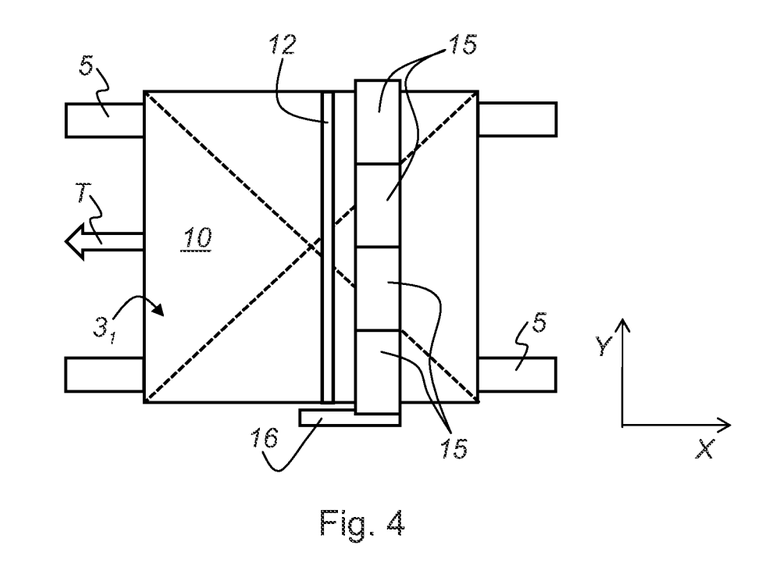
FIG. 4 shows a schematic top view of the arrangement of the second illumination system according to FIG. 2, wherein the substrate is in the X/Y-plane.

FIGS. 2 to 4 show a solution to overcome above mentioned drawback of intensity distribution and focus problem. FIG. 2 shows a schematic side view of the arrangement of the second illumination system 2 with respect to substrate 10 (wafer or solar cell). The second illumination system 2 comprises at least one light source 15 and a mounting 16 for providing support of the at least one light source 15 in order to be arranged above the front surface $3_1$ of substrate 10. The second illumination system 2 is tilted by a second angle δ with respect to the front surface $3_1$ of substrate 10. Consequently, light from the at least one light source 15 impinges onto the front surface $3_1$ of substrate 10 under the second angle δ. Substrate 10 is moved by the means 5 for moving in transport direction T.

FIG. 3 shows a schematic front view of the arrangement of the second illumination system 2 according to FIG. 2, wherein transport direction T of substrate 10 is perpendicular to the drawing plane. The second illumination system 2 is composed of four individual light sources 15. The four individual light sources 15 are attached to the mounting 16 such that a single and continuous second elongated spot 12 of light (see FIG. 4) is projected onto the front surface $3_1$ of substrate 10. The four individual light sources 15 forming the second illumination system 2 is one possible embodiment and should not be considered as a limitation of the invention. Each of the individual light sources 15 is arranged at a third angle β with respect to the second elongated spot 12 of light (see FIG. 1) on the front surface $3_1$ of substrate 10.

FIG. 4 shows a schematic top view of the arrangement of the second illumination system 2 according to FIG. 2, wherein substrate 10 is in the X/Y-plane defined by the Cartesian coordinate system (X,Y). The four individual line light sources 15 are supported by mounting 16. Together the light sources 15 project the second elongated spot 12 of light onto the front surface $3_1$ of substrate 10 while substrate 10 is moved by the means 5 for moving along transport direction T.

Figure 5:
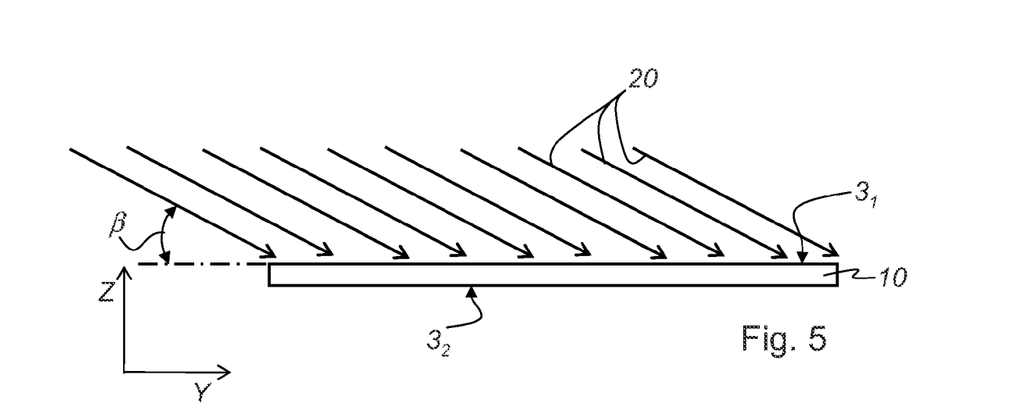
FIG. 5 shows a detailed view how the light from the second illumination system is shined onto the surface of the substrate.

FIG. 5 shows in detail how light 20 from the line light sources 15 (see FIG. 4) of the second illumination system 2 is shed onto the surface 31 of substrate 10. Light 20 includes the third angle β with the front surface 31 of substrate 10. The multiple light sources 15 as shown in FIG. 3 can be reduced in size and increased in number. In case the light sources are reduced to point light sources, the result is that the homogeneity across the elongated spot 12 of light is increased.

Figure 6:
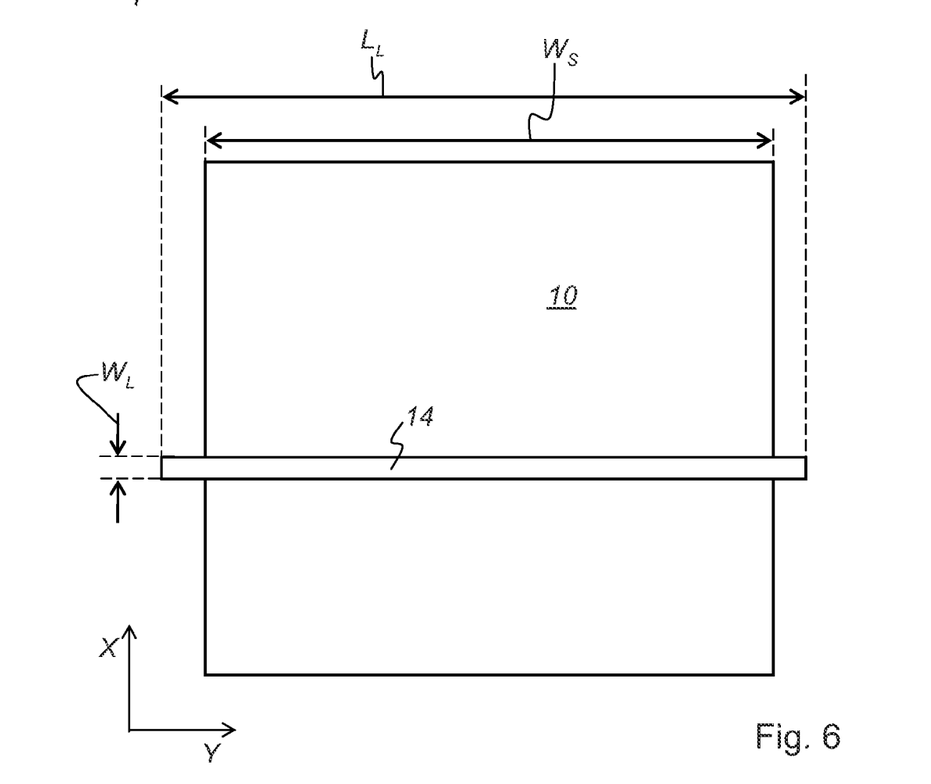
FIG. 6 shows a top view of the substrate and the illuminated area in the surface of the substrate.

FIG. 6 shows a top view of substrate 10. As mentioned above, substrate 10 could be a monocrystalline or polycrystalline bare wafer or a monocrystalline or polycrystalline semi of fully processed solar cell. Substrate 10 has a width W. The first line 11 or the second line 12 of light result in an illuminated area 14 on the front surface $3_1$ of substrate 10. The illuminated area 14 has a length $L_L$ and a width $W_L$, wherein the length $L_L$ of the illuminated area 14 is larger than the width $W_s$ of substrate 10. This dimensioning ensures that the entire front surface $3_1$ of substrate 10 is illuminated during the transport of substrate 10.

Figure 7:
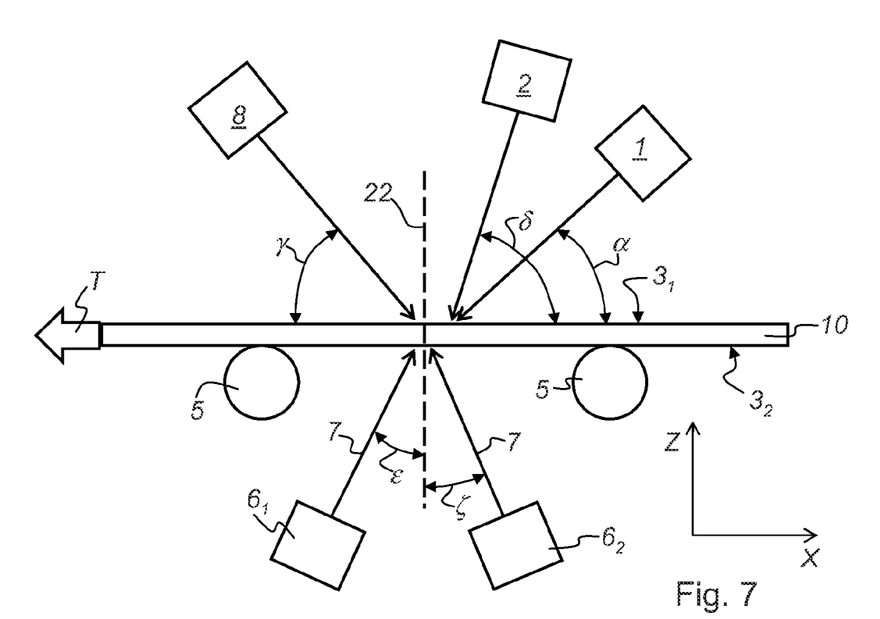
FIG. 7 shows a schematic side view of a further embodiment of the invention which uses three illumination systems in order to illuminate the substrate (wafer) under inspection.

FIG. 7 shows a schematic side view of a further embodiment of the invention which uses three illumination systems 1, 2 and 8 in order to illuminate substrate 10 under inspection. Beside the first illumination system 1 and the second illumination system 2 a third illumination system 8 is provided. The first illumination system 1, second illumination system 2 and the third illumination system 8 shine light onto the front surface $3_1$ of substrate 10. A first camera $6_1$ and a second camera $6_2$ view to the back surface $3_2$ of substrate 10. The second camera $6_2$ is preferably sensitive between 400 nm and 1200 nm. The second camera $6_2$ is adapted to capture the transmitted light shed from the third illumination system 8. The light from the third illumination system 8 is received by the second camera $6_2$ independently from the first illumination system 1 and the second illumination system 2. The setup described in FIG. 7 will allow visualization of those defects (penetrating micro cracks, pinholes and inclusions) that are not visualized by the setup as described in FIG. 1.

The first camera $6_1$ and the second camera $6_2$ face the back surface $3_2$ of substrate 10. Substrate 10 is as well transported by means 5 for moving along transport direction T. The first scan camera $6_1$ defines a first image capture field $4_1$ (see FIG. 10) on the back surface $3_2$ of substrate 10. The second camera $6_2$ defines a second image capture field $4_2$ (see also FIG. 10) on the back surface $3_2$ of substrate 10. The first camera $6_1$ and the second camera $6_2$ receive the light from the first illumination system 1 and light from the second illumination system 2 transmitted through the monocrystalline or polycrystalline substrate 10.

The third illumination system 8 is arranged such that the second camera 62 captures light transmitted from the third illumination system 8 through substrate 10. According to the embodiment shown in FIG. 7 the light from the first illumination system 1 and second illumination system 2 is projected to a first illuminated area $14_1$ (see FIG. 10) on the front surface $3_1$ of substrate 10. The light from the third illumination system 8 is projected to a second illuminated area $14_2$ (see also FIG. 10) on the front surface $3_1$ of substrate 10. The first illuminated area $14_1$ and the second illuminated area $14_2$ are positioned such on the front surface $3_1$ of substrate 10 that they do not interfere with the image capture field of the first camera $6_1$ and the second camera $6_2$. The spectra of the first illumination system 1, the second illumination system 2 and the third illumination system 8 should be chosen by relevant optical cut-off filters or choosing the appropriate light sources.

It is important to note that the first camera $6_1$ and the second camera $6_2$ are tilted with respect to a normal 22 of substrate 10 to be inspected. As shown by the embodiment described in FIG. 7, the first camera $6_1$ is tilted by a sixth angle with respect to the normal 22 of substrate 10. The second camera $6_s$ is tilted by a fifth angle £ with respect to the normal 22 of substrate 10. As already described with respect to FIG. 1, the light from the first illumination system 1 is directed to the front surface $3_1$ of substrate 10 under a first angle α. The light from the second illumination system 2 illuminates substrate 10 under a second angle δ with respect to the front surface $3_1$ of substrate 10. The third illumination system 8 shines light onto the front surface $3_1$ of substrate 10 under a fourth angle γ. The second camera $6_2$ captures the light from the third illumination system 8.

Figure 8:
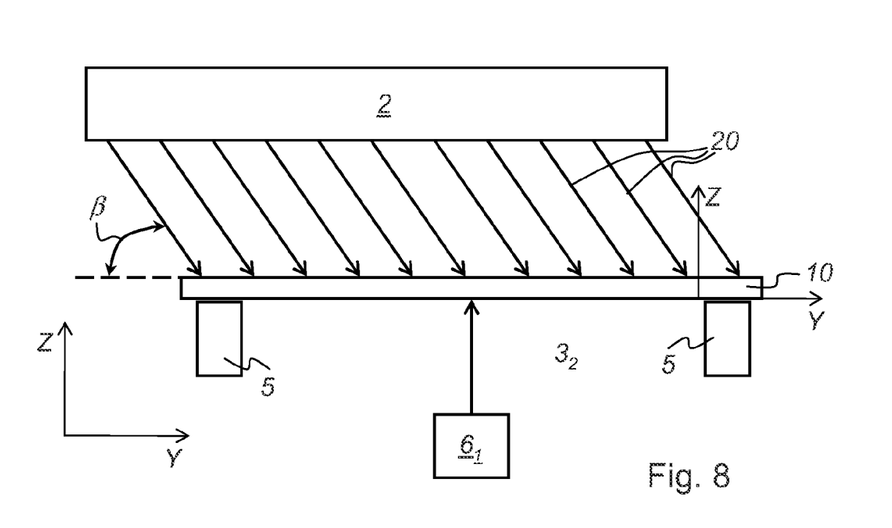
FIG. 8 shows a schematic front view of the arrangement of the second illumination system of the embodiment shown in FIG. 1, wherein the transport direction of the substrate is perpendicular to the drawing plane.

FIG. 8 shows a schematic front view (forward view) of the arrangement of the second illumination system 2 of the embodiment shown in FIG. 1, wherein the transport direction T of substrate 10 is perpendicular to the drawing plane. As already described in FIG. 1, the second illumination system 2 is arranged at a third angle β with respect to the front surface $3_1$ of substrate 10. Third angle β ranges between 5 to 30 degrees, but preferably third angle β ranges between 10 to 25 degrees with respect to the second line 12 of light. The arrangement of second illumination system 2 by third angle β is comparable to a street lamp. First camera $6_1$ is facing the back surface $3_2$ of substrate 10.

Figure 9:
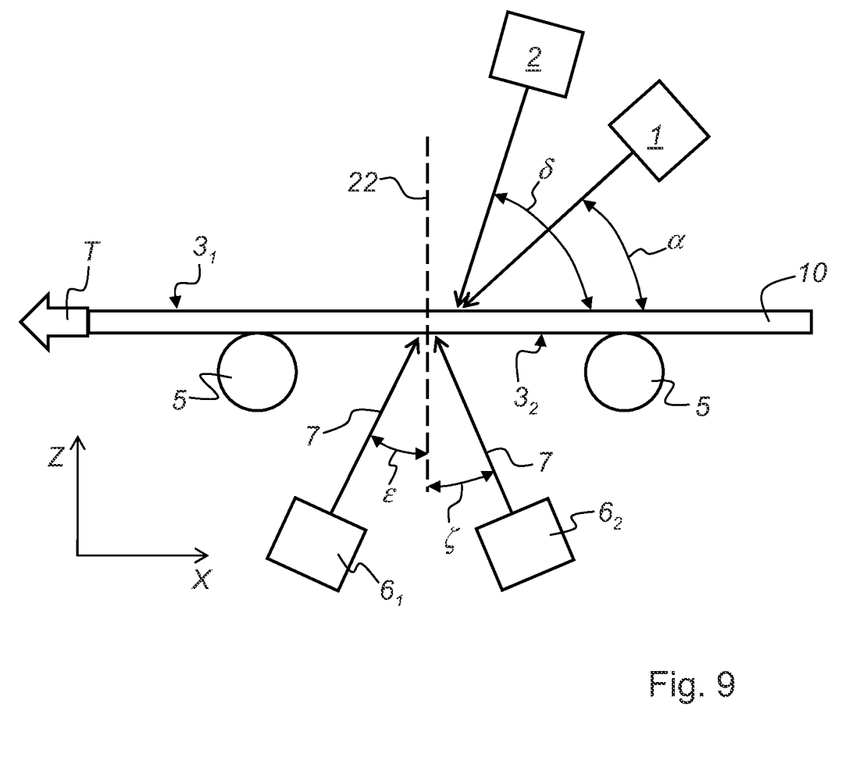
FIG. 9 shows a schematic side view of an embodiment of the invention which uses the first and second illumination systems of FIG. 1 and a first and a second camera to detect light transmitted through the substrate (wafer or solar cell)

FIG. 9 shows a schematic side view of an embodiment of the invention which uses the first illumination system 1 and the second illumination system 2 (already described in FIG. 1), configured as line light sources, and a first camera 61 and a second camera 62 to detect light transmitted through substrate 10 (monocrystalline or polycrystalline wafer). The third illumination system 8 (described in FIG. 7) is not used here. The detection capacity for non-penetrating defects, penetrating cracks, pinholes and inclusions would be maintained as in the case of the embodiment with the three illumination systems 1, 2, 8 (see FIG. 7). This could be done by an optimum alignment and positioning of first illumination system 1, second illumination system 2, first camera 61, and second camera 62. The first camera 61 and the second camera 62 are arranged opposite to the back surface 32 of substrate 10. As already described with respect to FIG. 1, the light from the first illumination system 1 is directed to the front surface 31 of substrate 10 under a first angle α. The light from the second illumination system 2 illuminates substrate 10 under a second angle δ with respect to the front surface 31 of substrate 10. Substrate 10 is transported along transport direction T. The proper detection for non-penetrating defects, penetrating cracks, pinholes and inclusions is achieved in that the first camera 61 captures the light from the first illumination system 1 and the second illumination system 2, whereas the second camera 62 captures light from the first illumination system 1 only.

Figure 10:
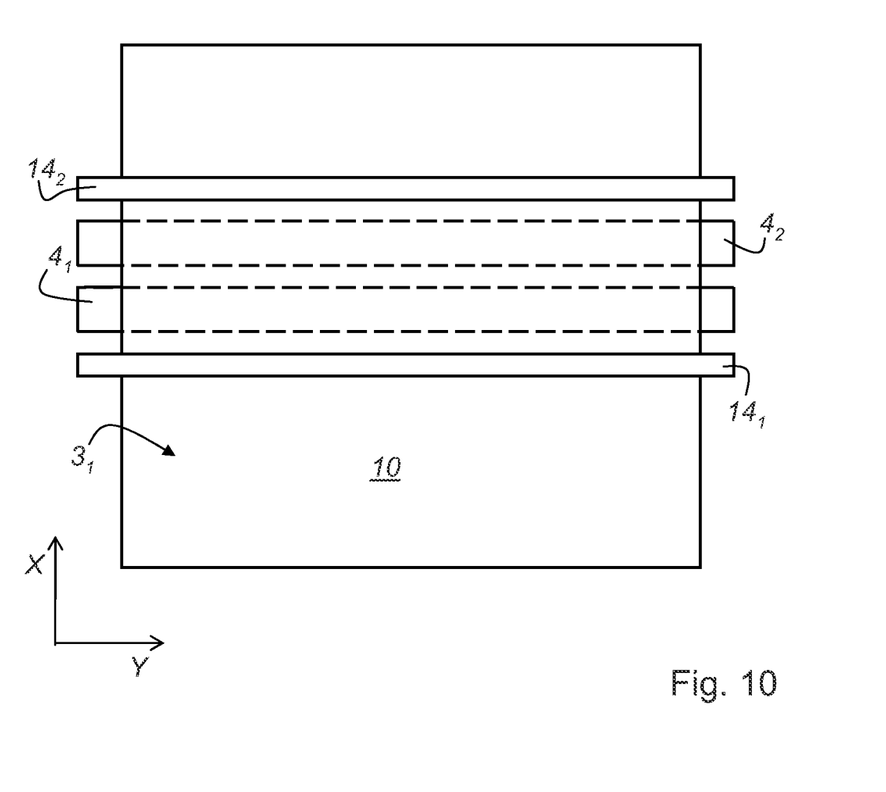
FIG. 10 shows a top view of the substrate and the possible positioning of the line shaped illumination and the image capture fields with respect to the substrate.

FIG. 10 shows a top view of substrate 10 and the possible positioning of the line shaped illumination areas $14_1$, $14_2$ and the image capture fields $4_1$, $4_2$ with respect to substrate 10. The arrangement of the first image capture field $4_1$ and the second image capture field $4_2$ as well as the first illuminated area $14_1$ and the second illuminated area $14_2$ are described with respect to the embodiment shown in FIG. 7. The first illuminated area $14_1$ and the second illuminated area $14_2$ are on the front surface $3_1$ of substrate 10. The first image capture field $4_1$ and the second image capture field $4_2$ are defined by the first camera $6_1$ and the second camera $6_2$ on the back surface $3_2$ of substrate 10 respectively.

Figure 11:
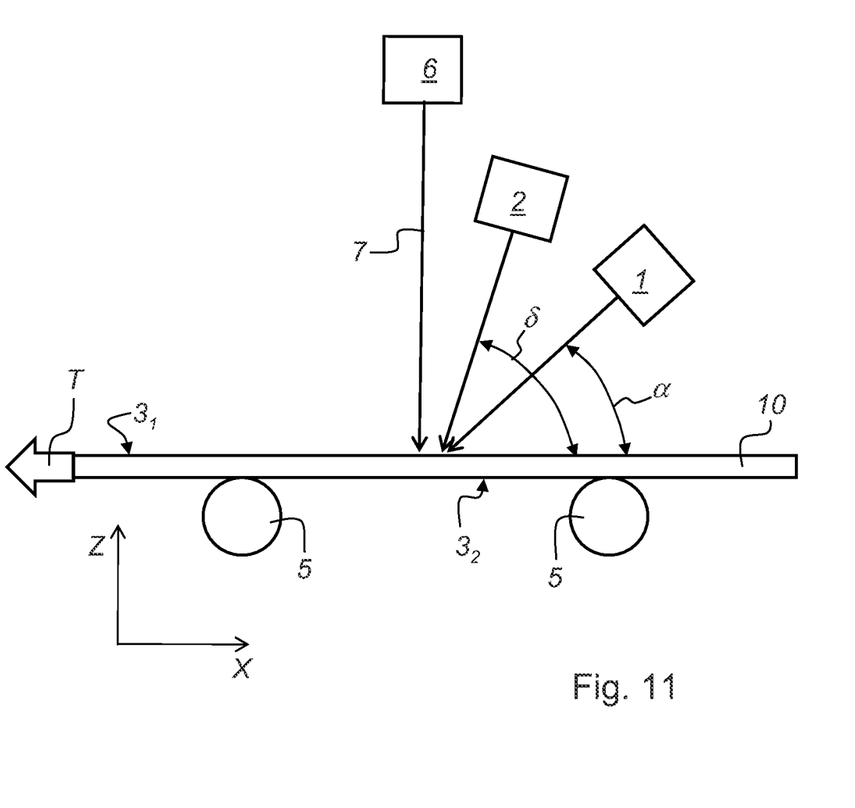
FIG. 11 shows an embodiment of the invention which is able to inspect non penetrating micro cracks in wafers and semi or fully finished solar cells.

FIG. 11 shows an embodiment of the invention which is able to inspect non-penetrating micro cracks in substrates 10, like wafers and semi or fully finished solar cells. The solar cells have different coatings including metallic electrode (not shown). The embodiment shown in FIG. 11 has a first illumination system 1 and a second illumination system 2, both of which are arranged according the setup disclosed in FIG. 1 or 9 and face the front surface $3_1$ of substrate 10. A camera 6 faces as well the front surface $3_1$ of substrate 10. According to the embodiment shown here, the optical axis 7 of camera 6 is arranged such that the camera 6 views to the front surface $3_1$ of substrate 10. With the setup shown here it is possible to resolve the orientation dependency of the micro cracks. Camera 6 captures light reflected from the inspected substrate 10. The embodiment shown in FIG. 11 can be practiced without the second illumination system 2. However, with this modification the orientation dependency of the micro cracks cannot be resolved.

Figure 12:
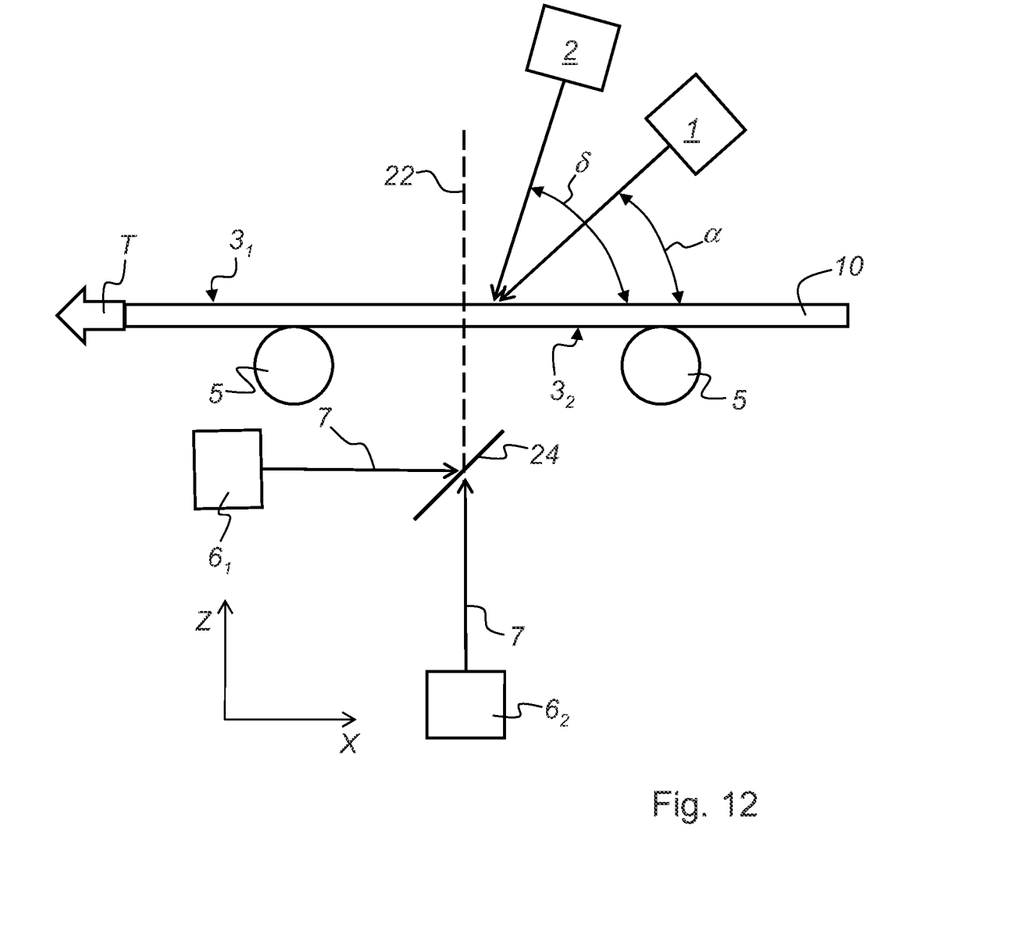
FIG. 12 shows a schematic side view of the embodiment as shown in FIG. 9 wherein the first and second camera to detect light transmitted through the substrate (wafer or solar cell) and are arranged differently.

FIG. 12 shows a schematic side view of a further modification of the arrangement of the first camera $6_1$ and the second camera $6_2$. The invention uses the first illumination system 1 and the second illumination system 2 (already described in FIG. 1). In the optical axis 7 of the first camera $6_1$ and the second camera $6_2$ an optical element 24 is positioned. The optical element 24 is adapted to direct the light transmitted through substrate 10 (monocrystalline or polycrystalline wafer) to the first camera $6_1$ and the second camera $6_2$, respectively. The optical element 24 is configured as a 50/50 mirror, a beam splitter, a dichroitic beam splitter or the like. The detection capacity for non-penetrating defects, penetrating cracks, pinholes and inclusions would be maintained as in the case of the embodiment with the three illumination systems 1, 2, 8 (see FIG. 7). This could be done by an optimum alignment and positioning of first illumination system 1, second illumination system 2, first camera $6_1$, and second camera $6_2$.

The invention has been described with reference to preferred embodiments. However, it is obvious for a person skilled in the art that modifications and alterations of the invention can be made without leaving the scope of the subsequent claims.

REFERENCE NUMERALS 1 first illumination system
2 second illumination system
2A axis of second illumination system
$3_1$ front surface
$3_2$ back surface
4 image capture field
$4_1$ first image capture field
$4_2$ second image capture field
5 means for moving
6 camera
$6_1$ first camera
$6_2$ second camera
7 optical axis
8 third illumination system
9 optical system
10 substrate
11 first elongated spot of light
12 second elongated spot of light
14 illuminated area
$14_1$ first illuminated area
$14_2$ second illuminated area
15 elongated light source
16 mounting of elongated light source
20 light
22 normal of the substrate
24 optical element
$L_L$ length of the illuminated area
T direction of transport
$W_L$ width of the illuminated area
$W_s$ width of the substrate
X X-direction
Y Y-direction
Z Z-direction α first illumination angle of first illumination system
β tilt angle of second illumination system (third angle)
δ second illumination angle of second illumination system
γ fourth illumination angle of third illumination system
ε tilt angle of first camera (fifth angle)
ζ tilt angle of second camera (sixth angle)

What is claimed is:

1. An apparatus for illuminating a substrate in order to image micro cracks, pinholes and inclusions in the substrate comprising:
   a conveyer unit to move the substrate along a transport direction;
   a first illumination system for illuminating a front surface of the substrate to create a first elongated spot of light on the front surface of the substrate, wherein the front surface of the substrate is defined by a first transport axis and a second transport axis, the first transport axis being parallel to the transport direction and the second transport axis being orthogonal to the transport direction, wherein the first elongated spot of light is oriented transverse to the transport direction, wherein the first illumination system is configured to illuminate the substrate at a first angle with respect to the first transport axis;
   a second illumination system for illuminating the front surface of the substrate to create a second elongated spot of light on the front surface of the substrate, wherein the second elongated spot of light is oriented transverse to the transport direction, the second illumination system is configured to illuminate the substrate at a second angle with respect to the first transport axis, wherein an axis of the second illumination system is arranged at a third angle with respect to the second transport axis; and
   an image capture field being defined on the substrate by the first elongated spot of light and the second elongated spot of light, the first elongated spot of light and the second elongated spot of light configured so as not to intersect at the front surface of the substrate and the image capture field during the movement of the substrate along the transport direction.

2. The apparatus of claim 1, wherein first and the second illumination system are configured as line light sources.

3. The apparatus of claim 2, wherein the line light source of the second illumination system is formed by a plurality of individual line light sources each of which are configured to shed light onto the substrate at the second angle with respect to the first transport axis, and an axis of each line light source is arranged at the third angle with respect to the second transport axis.

4. The apparatus of claim 1, wherein the image capture field is defined by at least one camera and the camera is sensitive to wavelength bands where the substrate is transparent.

5. The apparatus of claim 4, wherein the at least one camera is arranged such that the image capture field is defined on a back surface of the substrate, and the at least one camera is configured to receive the light from the first illumination system and the second illumination system, the light being transmitted through the substrate.

6. The apparatus of claim 1, wherein the first illumination system and the second illumination system provide light in a wavelength band where the substrate is transparent.

7. The apparatus of claim 1, wherein a first camera defines a first image capture field on a back surface of the substrate, and a second camera defines a second image capture field on the back surface of the substrate, wherein the first camera and the second camera are configured to receive the light from the first illumination system, and light from the second illumination system is transmitted through the substrate.

8. The apparatus of claim 7, wherein an optical axis of the first camera is arranged at a fourth angle with respect to a normal of the substrate, and an optical axis of the second camera is arranged at a fifth angle with respect to the normal of the substrate.

9. The apparatus of claim 7, wherein a third illumination system is arranged such that the second camera captures transmitted light from the third illumination system.

10. The apparatus of claim 1, wherein the image capture field is defined on the front surface of the substrate by a camera, and the camera is configured to receive light reflected from the front surface of the substrate.

11. The apparatus of claim 10, wherein the substrate is a semi or fully finished solar cell with different coatings and metallic electrodes on the front and rear surface.

12. The apparatus of claim 1, wherein the substrate comprises:
   at least one of a monocrystalline substrate or a polycrystalline substrate.

13. An apparatus for imaging non-penetrating micro cracks in wafers of solar cells comprising:
   a conveyor unit configured to move a solar cell along a transport direction, the solar cell comprising at least one substrate;
   a first illumination system for illuminating a front surface of the solar cell to create a first elongated spot of light on the front surface of the solar cell, wherein the front surface of the solar cell is defined by a first transport axis and a second transport axis, the first transport axis being parallel to the transport direction and the second transport axis being orthogonal to the transport direction, the front surface including coatings and metallic electrodes, wherein the first elongated spot of light is oriented transverse to the transport direction, wherein the first illumination system is configured to illuminate the solar cell at a first angle with respect to the first transport axis;
   a second illumination system for illuminating the front surface of the solar cell to create a second elongated spot of light on the front surface of the solar cell, wherein the second elongated spot of light is oriented transverse to the transport direction, the second illumination system is configured to illuminate the front surface of the solar cell at a second angle with respect to the first transport axis, wherein an axis of the second illumination system is arranged at a third angle with respect to the second transport axis, wherein the first elongated spot of light and the second elongated spot of light are configured so as not to intersect at the front surface of the solar cell; and
   a camera being arranged above the front surface of the solar cell and configured for capturing light reflected from the front surface of the solar cell during the movement of the solar cell along the transport direction.

14. The apparatus of claim 13, wherein the camera is a camera defining an image capture field on the front surface of the solar cell.

15. The apparatus of claim 13, wherein the solar cell comprises:
   at least one of a monocrystalline substrate or a polycrystalline substrate.

16. An apparatus for illuminating and imaging solar cell substrates in order to detect micro cracks, pinholes and inclusions in the substrates comprising:
   a conveyor unit configured to move a substrate along a transport direction;

a first illumination system for illuminating a front surface of the substrate to create a first elongated spot of light on the front surface of the substrate, wherein the front surface of the substrate is defined by a first transport axis and a second transport axis, the first transport axis being parallel to the transport direction and the second transport axis being orthogonal to the transport direction, wherein the first elongated spot of light is oriented transverse to the transport direction, wherein the first illumination system is configured to illuminate the substrate at a first angle with respect to the first transport axis;

a second illumination system for illuminating the front surface of the substrate to create a second elongated spot of light on the front surface of the substrate, wherein the second elongated spot of light is oriented transverse to the transport direction, the second illumination system is configured to illuminate the substrate at a second angle with respect to the first transport axis, wherein an axis of the second illumination system is arranged at a third angle with respect to the second transport axis;

a first camera configured for defining a first image capture field, and a second camera configured for defining a second image capture field, wherein the first image capture field and the second image capture field are defined at the back surface of the substrate by the first and second elongated spots of light, the first elongated spot of light and the second elongated spot of light configured so as not to intersect at the front surface of the substrate or at the second image capture field; and the first and the second camera configured for receiving the light from the first illumination system, and light from the second illumination system being transmitted through the substrate.

17. The apparatus of claim 16, wherein an optical axis of the first camera is arranged at a fourth angle with respect to the normal of the back surface of the substrate, and an optical axis of the second camera is arranged at a fifth angle with respect to the normal of the back surface of the substrate, and wherein the first camera is configured for receiving the light from the first illumination system and the light from the second illumination system, and the second camera is configured for receiving only the light from the first illumination system.

18. The apparatus of claim 16, wherein the first illumination system and the second illumination system are configured as line light sources.

19. The apparatus of claim 16, wherein the line light source of the second illumination system is formed by a plurality of individual line light sources each of which are configured to illuminate the front side of the substrate at the second angle with respect to the first transport axis, and wherein an axis of each line light source is arranged at the third angle with respect to the second transport axis.

20. The apparatus of claim 16, wherein a third illumination system is arranged such that the second camera captures transmitted light from the third illumination system through the substrate.

21. The apparatus of claim 16, wherein the first camera is configured for receiving the light from the first illumination system and the second illumination system, and wherein the second camera is configured for receiving the light only from the first illumination system.

22. The apparatus of claim 19, wherein the third illumination system is configured as a line light source.

23. A method for imaging micro cracks, pinholes or inclusions in substrates comprising:

moving a substrate along a transport direction;

illuminating a front surface of the moving substrate to create a first elongated spot of light on the front surface of the moving substrate, wherein the front surface of the moving substrate is defined by a first transport axis and a second transport axis, the first transport axis being parallel to the transport direction and the second transport axis being orthogonal to the transport direction, wherein the first elongated spot of light is oriented transverse to the transport direction, wherein the first elongated spot of light illuminates the substrate at a first angle with respect to the first transport axis, the first elongated spot of light forming a first line on the surface of the substrate, the first elongated spot of light illuminated by a first illuminating system;

illuminating the front surface of the moving substrate to create a second elongated spot of light on the front surface of the substrate, the second elongated spot of light forming a second line on the surface of the substrate, the second elongated spot of light illuminated by a second illuminating system, wherein the second elongated spot of light is oriented transverse to the transport direction and the second elongated spot of light illuminates the substrate at a second angle with respect to the first transport axis, wherein an axis of the second illumination system is arranged at a third angle with respect to the second line and the second transport axis; and defining an image capture field by the first elongated spot of light and the second elongated spot of light, the first elongated spot of light and the second elongated spot of light configured so as not to intersect at the front surface of the substrate and the image capture field of at least one camera during the movement of the substrate along the transport direction.

24. The method of claim 23, wherein the at least one camera is arranged such that the image capture field is defined on a back surface of the substrate, and the at least one camera is configured to receive the light from the first illumination system and second illumination system being transmitted through the substrate.

25. The method of claim 23, wherein the at least one camera is arranged such that the image capture field is defined on a front surface of the substrate, and the at least one camera is configured to receive the light from the first illumination system or the second illumination system, the light being reflected from the front surface of the substrate.

26. The method of claim 23, further comprising:

positioning an optical element to direct light transmitted through the substrate to the at least one camera and a second camera, the at least one camera having an optical axis in parallel with the front surface of the moving substrate, the second camera having an optical axis orthogonal to the front surface of the moving substrate, and wherein the optical element is a beam splitter.

* * * * *